United States Patent [19]

Fischer

[11] Plant 4,972

[45] Jan. 11, 1983

[54] AFRICAN VIOLET NAMED AURORA

[75] Inventor: Arnold W. Fischer, Hanover, Fed. Rep. of Germany

[73] Assignee: Pan American Plant Company, Parrish, Fla.

[21] Appl. No.: 252,836

[22] Filed: Apr. 10, 1981

[51] Int. Cl.[3] ..... A01H 5/00

[52] U.S. Cl. ..... Plt./69

[58] Field of Search ..... Plt./69

[56] References Cited

U.S. PATENT DOCUMENTS

P.P. 4,546 6/1980 Holtkamp ..... Plt./69

*Primary Examiner*—James R. Feyrer

*Attorney, Agent, or Firm*—Chas. W. Rummler

[57] ABSTRACT

A new and very distinct African Violet plant distinguished by its large zygomorphic-rotate flowers which have up to seven petals of a deep purple color, each trimmed with a narrow white marginal edge. This new plant has a vigorous growth habit and blooms profusely with strong stems to hold its unique flowers high above a medium green foliage.

4 Drawing Figures

BACKGROUND OF THE NEW PLANT

This unique African Violet cultivar originated as a seedling of unknown parentage discovered by me among a group of violet plants being maintained at Fallbrook, Calif., for the production of new and distinctive varieties of African Violet plants. This plant was discovered by me at Fallbrook in 1977 and because of its unique deep purple, white edged flowers, I selected this plant for propagation and test and by means of cuttings, I reproduced the discovery plant at Fallbrook with very favorable results. Subsequently, this new plant was propagated through many successive generations, which demonstrated that the novel characteristics of the plant would hold true from generation to generation and appeared to be firmly fixed. This cultivar is now being propagated on a commercial scale at West Chicago, Ill., and at Parrish, Fla.

DESCRIPTION OF THE DRAWINGS

This new violet plant is illustrated by the accompanying drawings, of which sheet 1 is a full color photographic view of a potted plant in full bloom, sheet 2 is a photographic print showing face views of several flowers of this variety which have been hand-painted to show the true flower colors, and sheets 3 and 4 are prints of machine copies of the front and back sides, respectively, of typical leaves of this plant.

DESCRIPTION OF THE NEW PLANT

The following is a detailed description of this new African Violet cultivar based upon observations of greenhouse grown flowers at West Chicago, Ill., the color designations being according to The R.H.S. Colour Chart published by The Royal Horticultural Society of London, England.

THE PLANT

Origin: Seedling.
Parentage: Unknown.
Classification:
- *Botanic.*—Saintpaulia Ionantha.
- *Commercial.*—African Violet.

Form: Compact and of rosette shape.

Growth: Vigorous.
Growth rate: Normal.
Foliage:
- *Quantity.*—Medium, about 16 leaves.
- *Size of leaf.*—Length — From insignificant to about 85 mm. Width — From insignificant to about 80 mm.
- *Shape of leaf.*—Oval with a rounded to acute tip, a cordate base and repand margins.
- *Texture.*—Pubescent.
- *Aspect.*—Glossy.
- *Color.*—Upper side — 137A. Under side — 138D.
- *Ribs and veins.*—Pinnate.
- *Rachis.*—From insignificant to about 85 mm. long.
- *Petioles.*—Length — From insignificant to about 100 mm.

THE BUD

Form: Globular.
Size: Average with various diameters and lengths.
Opening rate: Typical violet.
Color of petals:
- *When sepals first divide.*—89D.
- *When petals begin to unfurl.*—89A.

Sepals:
- *Number.*—Five.
- *Shape.*—Lanceolate and branched.
- *Color.*—Inside — 199B.
- *Striae.*—None.

Calyx:
- *Size.*—Small.
- *Shape.*—Calyx splits to star shape.
- *Aspect.*—Hairy.

Peduncle:
- *Character.*—Rigid and erect.
- *Length.*—From insignificant to about 90 mm.
- *Aspect.*—Hairy.
- *Color.*—199C.

THE FLOWER

Blooming habit: Intermittent.
Flowering: Profusely.
Flower size: Large.
- *Diameter.*—About 32 to 42 mm.

*Depth.*—Flat.

Borne: As a cyme.

Shape: Cup-shaped when bloom first opens, becoming flat as bloom matures.

Petalage:

*Number of petals.*—Six to seven.

*Arrangement.*—Sympetalous.

*Form.*—Zygomorphic-rotate with rounded apex and repand margins.

*Texture.*—Soft.

*Appearance.*—Satiny.

*Color.*—Petal body — 89A. Petal edging — 155D. Reverse side — 89D.

*Petaloids.*—From none to a few.

Flower stem:

*Character.*—Strong and upright.

*Length.*—From insignificant to about 90 mm.

*Color.*—199C.

Persistence: Flowers hang on and dry.

Fragrance: None.

Lasting quality: From 10 to 20 days on the plant.

REPRODUCTIVE ORGANS

Stamens:

*Anthers.*—Number: Four. Arrangement: Monadelphous. Size: About 3 mm. square. Color: Yellow.

*Filaments.*—Length: About 3 mm. Color: Whitish yellow.

*Pollen.*—Color — Yellow.

Pistils:

*Number.*—One.

*Style.*—Length: About 7 mm. Color: 89A.

*Stigma.*—Color — Whitish.

Ovaries: Hypogynous and tomentose.

This new African Violet plant is particularly distinguished by its unique deep purple flowers, the petals of which are trimmed with white. Each zygomorphic flower has up to seven petals and the flower mass is supported on strong stems high above a bed of medium green foliage. The plant has a vigorous growth habit and its flowers are of good substance with excellent keeping quality.

I claim:

1. A new and distinct African Violet plant, substantially as herein shown and described, characterized by its profuse production of deep purple flowers, each flower having its petals trimmed with a narrow edging of white.

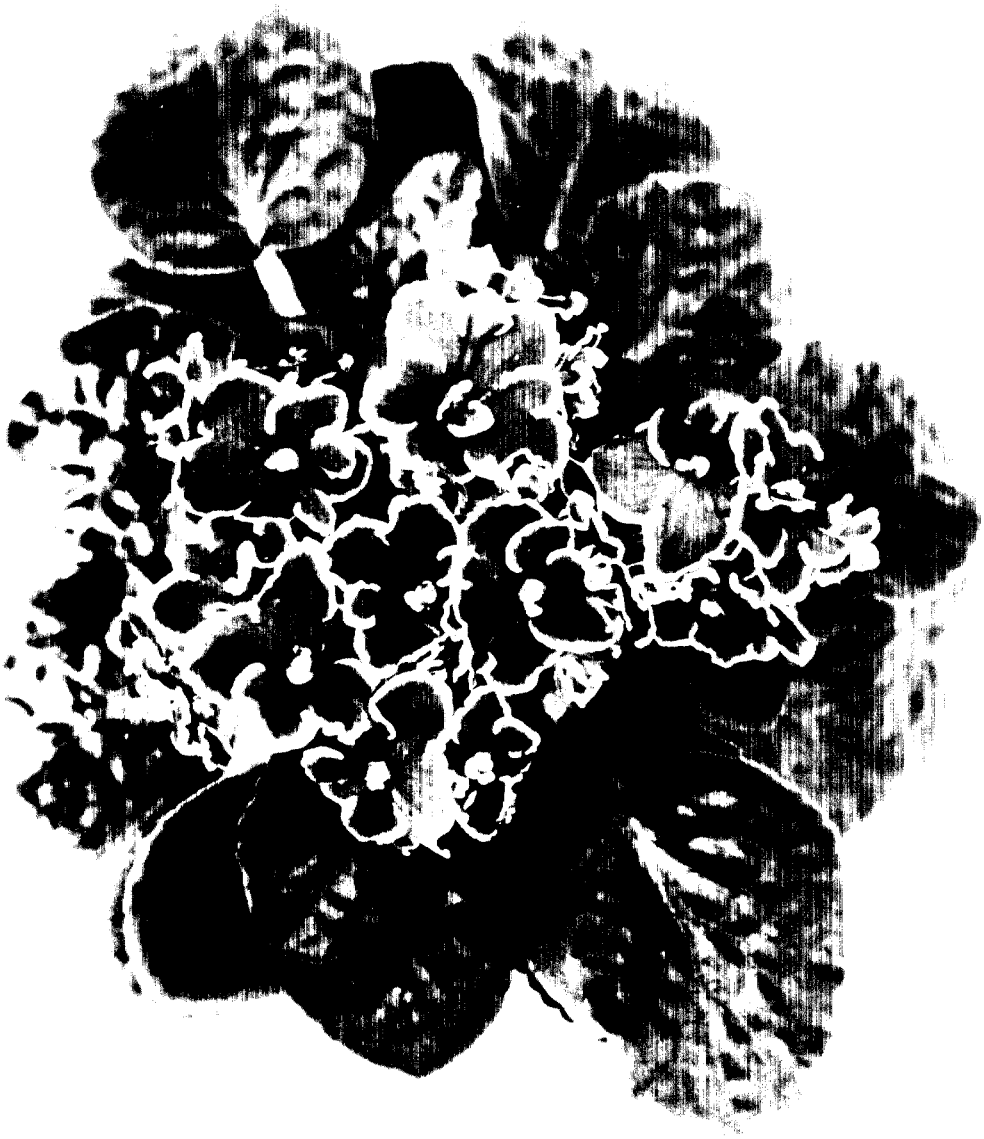

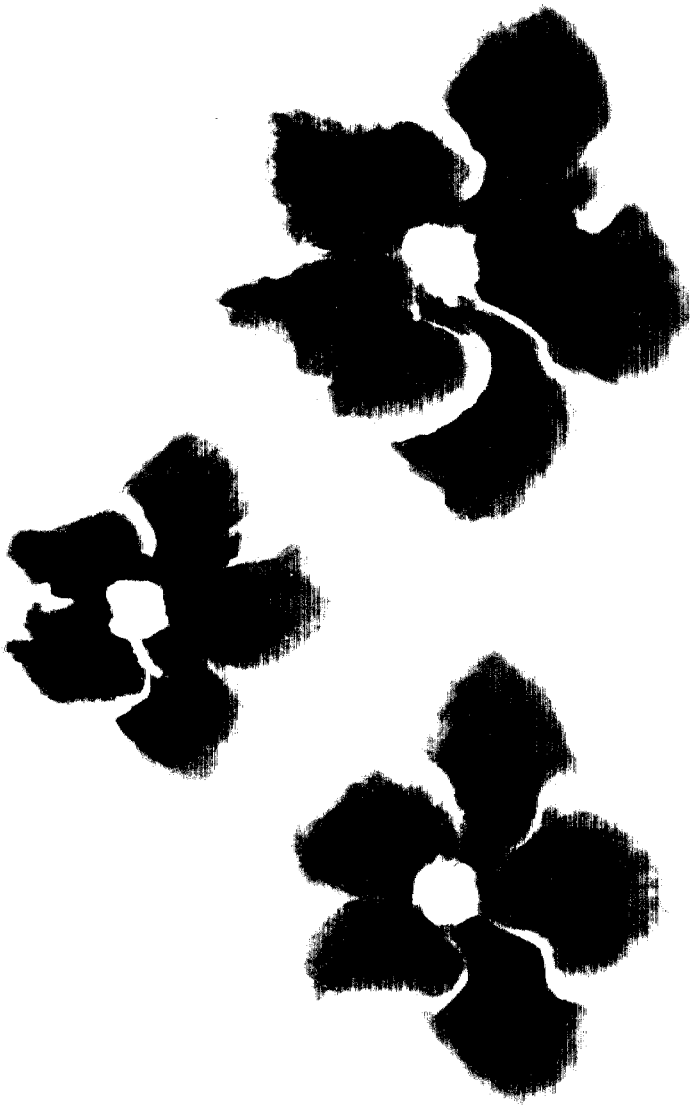

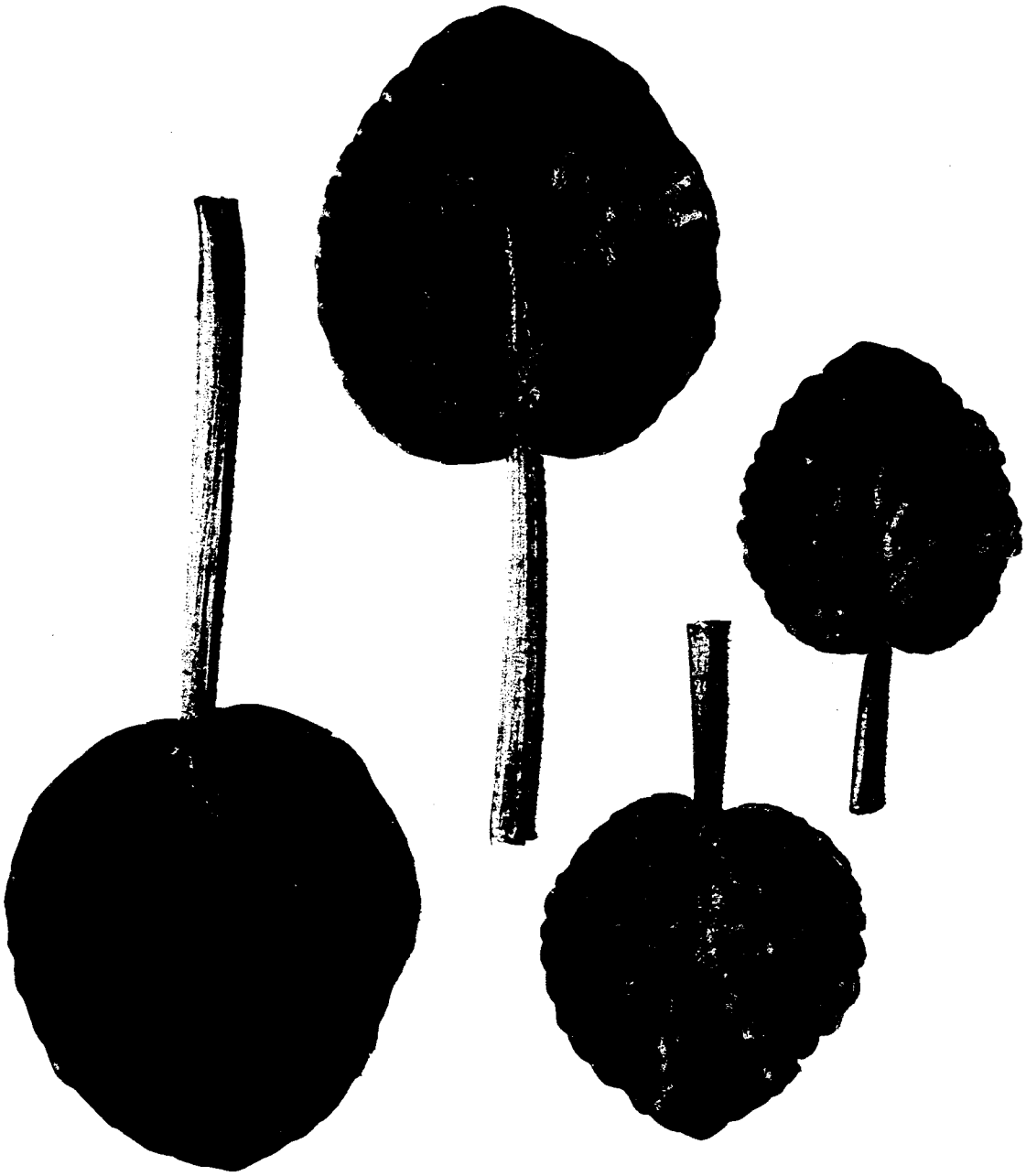

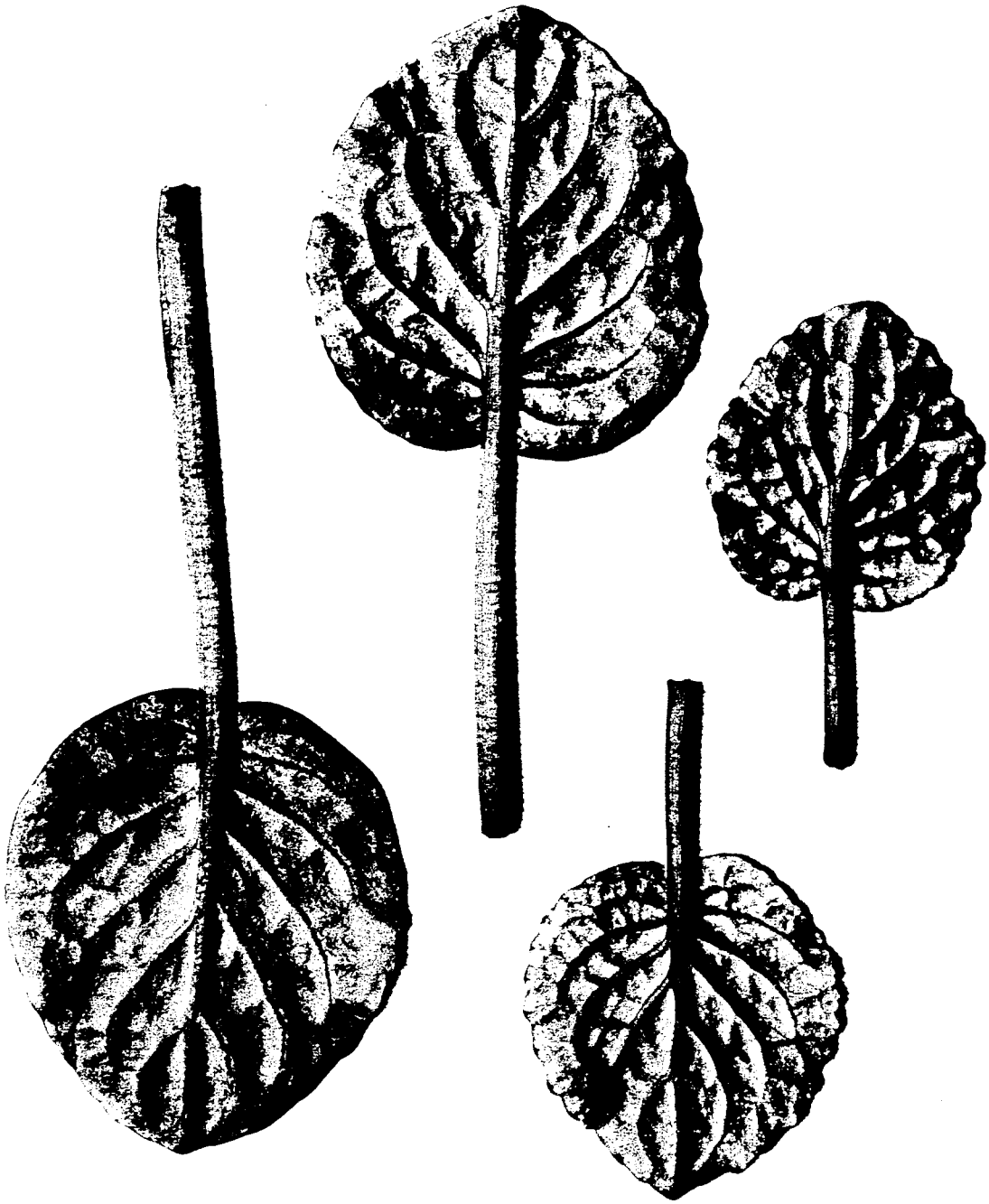

* * * * *